(12) United States Patent
Son et al.

(10) Patent No.: US 7,344,820 B2
(45) Date of Patent: Mar. 18, 2008

(54) CHEMICALLY AMPLIFIED POLYMER HAVING PENDANT GROUP WITH DICYCLOHEXYL AND RESIST COMPOSITION COMPRISING THE SAME

(75) Inventors: Eun-Kyung Son, Hwaseong (KR); Jae-Hyun Kang, Hwaseong (KR); Deog-Bae Kim, Hwaseong (KR); Jae-Hyun Kim, Hwaseong (KR)

(73) Assignee: DongJin Semichem Co., Ltd., Seo-Ku, Incheon (KR)

( * ) Notice: Subject to any disclaimer, the term of this patent is extended or adjusted under 35 U.S.C. 154(b) by 236 days.

(21) Appl. No.: 10/533,936

(22) PCT Filed: Nov. 19, 2002

(86) PCT No.: PCT/KR02/02157

§ 371 (c)(1),
(2), (4) Date: May 4, 2005

(87) PCT Pub. No.: WO2004/042477

PCT Pub. Date: May 21, 2004

(65) Prior Publication Data

US 2006/0019192 A1    Jan. 26, 2006

(30) Foreign Application Priority Data

Nov. 4, 2002    (KR) .................... 10-2002-0067882

(51) Int. Cl.
*G03F 7/004* (2006.01)
*C08F 232/04* (2006.01)
*C07C 69/753* (2006.01)

(52) U.S. Cl. .................. 430/270.1; 430/905; 430/910; 526/269; 526/281; 526/308; 560/118; 560/128

(58) Field of Classification Search .............. 430/270.1, 430/905, 910; 526/269, 281, 308; 560/118, 560/128

See application file for complete search history.

(56) References Cited

U.S. PATENT DOCUMENTS 5,968,713 A    10/1999    Nozaki et al. ............... 430/326
6,420,082 B1 *    7/2002    Sato et al. ................ 430/270.1
6,576,392 B1 *    6/2003    Sato et al. ................ 430/270.1

FOREIGN PATENT DOCUMENTS

| JP | 1996-101509 | 4/1996 |
| KR | 2001-40033 | 5/2001 |
| KR | 2001-85567 | 9/2001 |
| KR | 2002-47866 | 6/2002 |

* cited by examiner

*Primary Examiner*—John S. Chu
(74) *Attorney, Agent, or Firm*—Occhiuti Rohlicek & Tsao LLP

(57) ABSTRACT

The present invention relates to a chemically amplified polymer having a pendent group with dicyclohexyl bonded thereto, a process for the preparation thereof, and a resist composition comprising it, and more particularly, to a novel (meth)acrylic or norbornene carboxylate compound with dicyclohexyl bonded thereto, a process for the preparation thereof, a chemically amplified polymer synthesized therewith, and a positive photoresist composition for ArF comprising said polymer, with high resolution and excellent etching resistance.

16 Claims, 2 Drawing Sheets

CHEMICALLY AMPLIFIED POLYMER HAVING PENDANT GROUP WITH DICYCLOHEXYL AND RESIST COMPOSITION COMPRISING THE SAME

BACKGROUND OF THE PRESENT INVENTION (a) Field of the Present Invention

The present invention relates to a novel (meth)acrylic or norbornene carboxylate compound having a pendent group with dicyclohexyl bonded thereto, a process for the preparation thereof, a chemically amplified polymer synthesized therewith, and a photoresist composition for ArF comprising said polymer, with high resolution and excellent etching resistance.

(b) Description of the Related Art

As semiconductor devices become highly integrated, ultra-fine patterns having sub-quarter micron dimensions are needed. For this, the wavelengths of light sources used in patterning have become shortened according to Rayleigh's rule, such as from 436 nm (g-line) and 365 nm (1-line) to 193 nm (ArF), 157 nm (VUV), and 248 nm (KrF). In prior arts, however, in order to obtain a pattern size for devices having capacities exceeding 1 Gbit, general resist materials had to be used at 248 nm. Therefore, new resists capable of functioning at a shorter wavelength of 193-nm have been continuously developed to satisfy the requirements of fine resolution.

As is widely known, polymers for use as an ArF-resist material are classified according to their structure into three forms, polyacrylate, cycloolefin-maleic anhydride copolymer, and polynorbornene. Of them, the cycloolefin-maleic anhydride copolymer (COMA)-type resists are useful in view of more or less lithographic performances (pattern collapse, line edge roughness, SEM beam contraction, etching resistance, etc.) However, said COMA-based photoresists cause unsatisfactory results in resolution, especially in terms of line density and space pattern, due to the hydrolysis of maleic anhydride (MA). Also, photoresists comprising conventional COMA do not exhibit sufficient resistance and consequently a dry etching process is still difficult.

SUMMARY OF THE PRESENT INVENTION

Therefore, it is an object of the present invention to provide a (meth)acrylic carboxylate compound or norbornene carboxylate having a bulky aliphatic ring substituent capable of increasing high resolution and etching resistance and a process for the preparation thereof, in order to solve the problems of the prior arts as described above.

It is an another object of the present invention to provide a photosensitive copolymer and terpolymer suitable to be used for a chemically amplified resist, comprising a pendent group having a cyclic structure and aliphatic ring compound capable of obtaining sufficient resolution for the high integration of semiconductors and exhibiting sufficiently strong resistance to dry etching.

It is still another object of the present invention is to provide a chemically amplified positive photoresist composition for ArF comprising said photosensitive copolymer, terpolymer, and a mixture thereof.

To achieve the aforementioned objects, the present invention provides 1-alkyl-1-dicyclohexyl (meth)acrylate represented by the following formula 1:

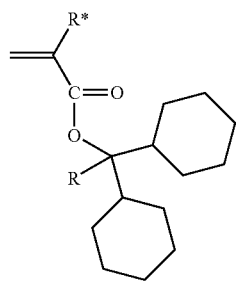

[Formula 1]

wherein R is a methyl or ethyl group, and R* is a hydrogen or a methyl group.

The present invention also provides a process for preparing 1-alkyl-1-dicyclohexyl (meth)acrylate of said formula 1, comprising the steps of:

a) preparing 1-alkyl-1-dicyclohexyl alcohol by the reaction of dicyclohexyl ketone and an alkyl grinard reagent or alkyl lithium reagent; and b) reacting the 1-alkyl-1-dicyclohexyl alcohol prepared above with (meth)acryloyl chloride.

The present invention also provides 2-alkyl-2-dicyclohexyl-5-norbornene-2-carboxylate represented by the following formula 2:

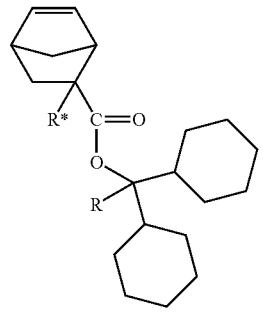

[Formula 2]

wherein R is a methyl or ethyl group, and R is a hydrogen or a methyl group.

Further, the present invention provides a process for preparing 2-alkyl-2-dicyclohexyl-5-norbornene-2-carboxylate of said formula 2 by the Diels-Alder reaction of 1-alkyl-1-dicyclohexyl (meth)acrylate of formula 1 and cyclopentadiene.

Still further, the present invention provides a photosensitive copolymer represented by the following formula 3:

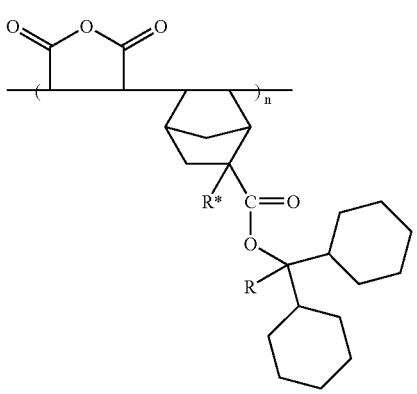

[Formula 3]

wherein R is a methyl or ethyl, R* is a hydrogen or a methyl, and n is an integer of 20 to 25.

Still further, the present invention provides a process for preparing the photosensitive copolymer of said formula 3 comprising the step of polymerizing the compound of said formula 2 with a maleic anhydride.

Also, the present invention provides a photosensitive terpolymer represented by the following formula 4:

[Formula 4]

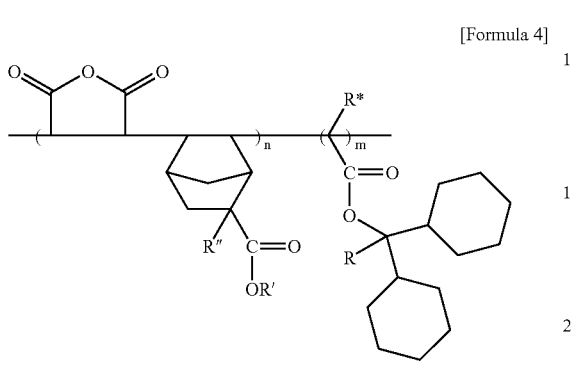

wherein R is a methyl or ethyl group; R* is a hydrogen or a methyl group; R' is a hydrogen, an alkyl group, or a hydroxyalkyl group; R" is a hydrogen or a methyl group; and m and n each satisfy the conditions m+n=1, 0.1<m<0.9 and 0.1<n<0.9.

Also, the present invention provides a process for preparing the photosensitive terpolymer of said formula 4 comprising the step of polymerizing the compound of formula 1 with a maleic anhydride and a norbornene compound of the following formula 6:

[Formula 6]

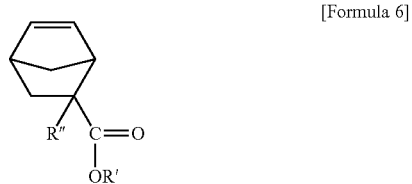

wherein R' is a hydrogen, an alkyl group, or a hydroxyalkyl group, and R" is a hydrogen or a methyl group.

Further, the present invention provides a photosensitive terpolymer represented by the following formula 5:

[Formula 5]

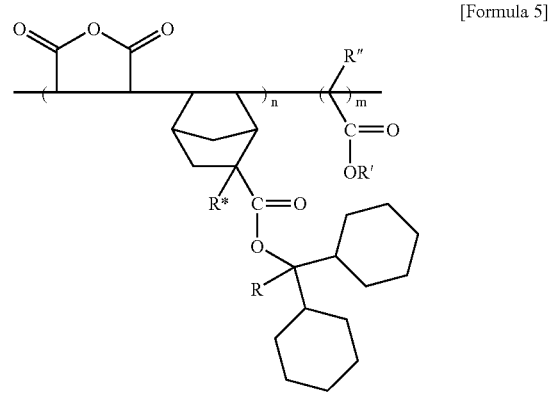

wherein R is a methyl or ethyl group; R* is a hydrogen or a methyl group; R' is a hydrogen, an alkyl group, or a hydroxyalkyl group; R" is a hydrogen or a methyl group; and m and n each satisfy the conditions m+n=1, 0.1<m<0.9 and 0.1<n<0.9.

Further, the present invention provides a process for preparing the photosensitive terpolymer of said formula 5 comprising the step of polymerizing the compound of formula 2 with a maleic anhydride and an acrylate compound of the following formula 7:

[Formula 7]

wherein R' is a hydrogen, an alkyl group, or a hydroxyalkyl group, and R" is a hydrogen or a methyl group.

Furthermore, the present invention provides a chemically amplified positive photoresist composition for ArF comprising one or more polymers selected from the group consisting of the photosensitive copolymer of formula 3, the photosensitive terpolymer of formula 4, and the photosensitive terpolymer of formula 5.

More particularly, in the formulae defined above, it is preferred that R' is an alkyl group having an aliphatic hydrocarbon of $C_1$-$C_{10}$ or a hydroxyalkyl group having an aliphatic hydrocarbon of $C_1$-$C_{10}$.

Also, the present invention provides a semiconductor device prepared comprising the above positive photoresist composition for ArF.

DETAILED DESCRIPTION AND THE PREFERRED EMBODIMENTS

Figure 1:
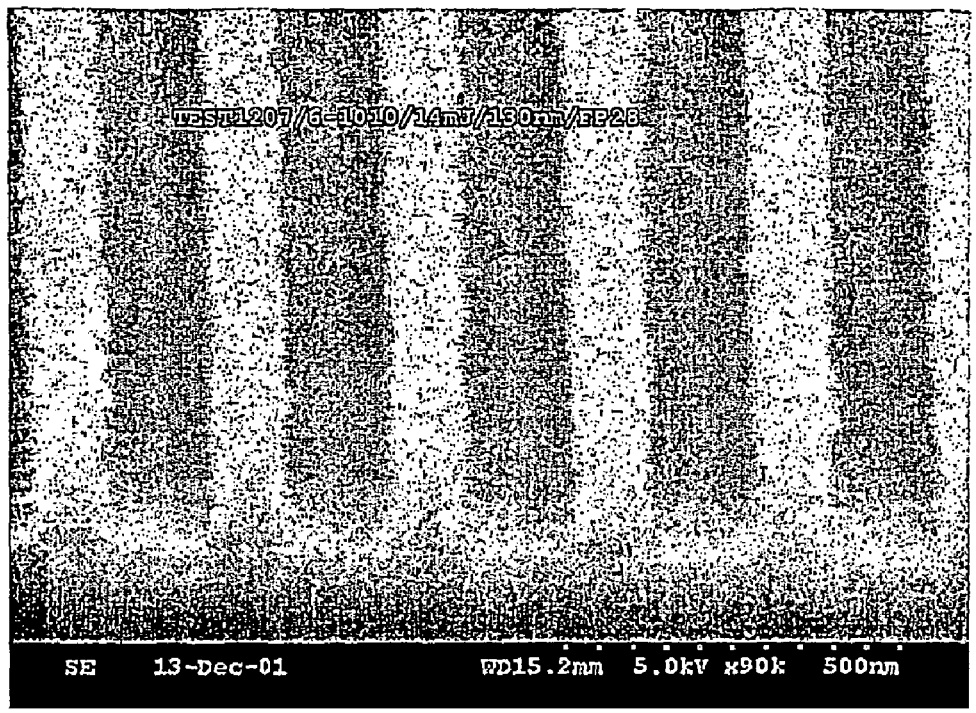
FIG. 1 illustrates a resist pattern in Example 7 according to the present invention.

The present invention is hereinafter described in detail.

The present invention provides preparation of a photosensitive copolymer and terpolymer using a (meth)acrylic carboxylate compound or norbornene carboxylate compound having a bulky aliphatic ring substituent, and a chemically amplified positive photoresist composition using said copolymer and terpolymer, which has high resolution and is excellent in etching resistance.

1-Alkyl-1-dicyclohexyl (meth)acrylate of formula 1 of the present invention can be prepared by reacting 1-alkyl-1-dicyclohexyl alcohol and (meth)acryloyl chloride.

The preparation of said 1-alkyl-1-dicyclohexyl alcohol follows the following Scheme 1:

[Scheme 1]

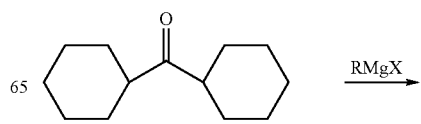

-continued

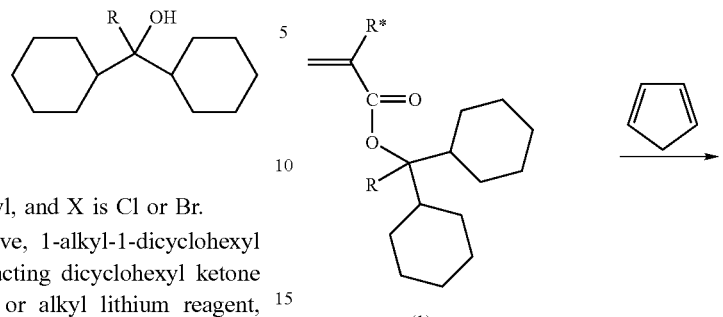

wherein R is a methyl or ethyl, and X is Cl or Br.

As shown in Scheme 1 above, 1-alkyl-1-dicyclohexyl alcohol can be prepared by reacting dicyclohexyl ketone with an alkyl grinard reagent or alkyl lithium reagent, thereby inducing an alkyl group on position 1 of dicyclohexyl ketone. The above grinard reagent includes alkyl magnesium bromide, alkyl magnesium chloride, etc., and more preferably, methyl magnesium bromide or methyl magnesium chloride is used.

Thereafter, according to the present invention, 1-alkyl-1-dicyclohexyl (meth)acrylate can be prepared by reacting 1-alkyl-1-dicyclohexyl alcohol and (meth)acryloyl chloride, as shown in the following Scheme 2:

[Scheme 2]

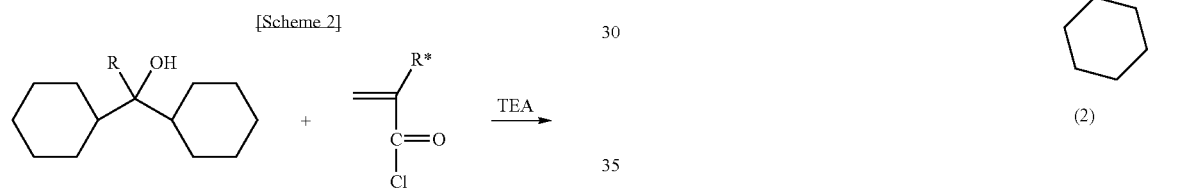

(1)

wherein R is a methyl or ethyl, and R* is a hydrogen or a methyl.

Also, according to the present invention, the norbornene compound of formula 2 can be prepared using the compound of formula 1.

According to the present invention, 2-alkyl-2-dicyclohexyl-5-norbornene-2-carboxylate of formula 2 having the norbornene substituent can be prepared by the Diels-Alder reaction of the compound of formula 1 and cyclopentadiene, as shown in the following scheme 3:

[Scheme 3]

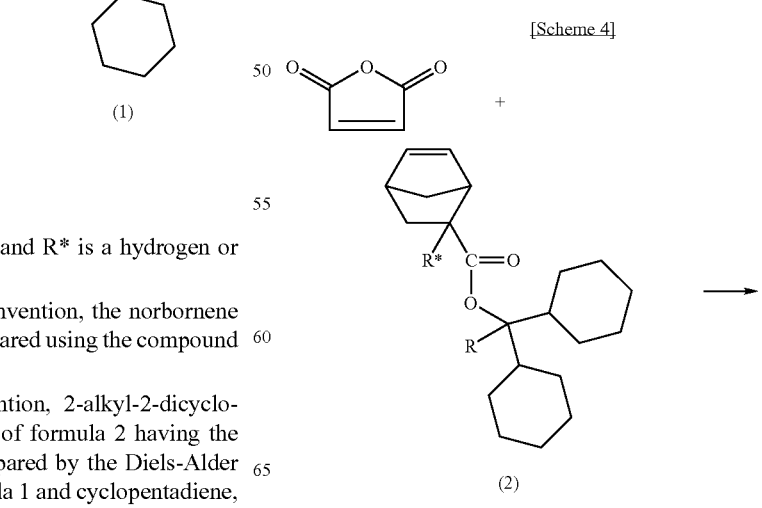

wherein R is a methyl or ethyl, and R* is a hydrogen or a methyl.

Also, according to the present invention, the photosensitive copolymer of formula 3 and the photosensitive terpolymers of formula 4 and 5 can be prepared using the compounds of formula 1 and formula 2.

First, the preparation of the photosensitive copolymer of formula 3 is as follows:

[Scheme 4]

-continued

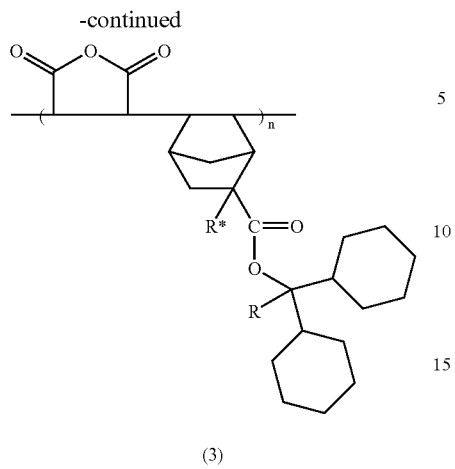

(3)

wherein R, R*, and n are as defined above.

As shown in scheme 4 above, the photosensitive copolymer of formula 3 can be obtained by polymerizing the norbornene compound of formula 2 with a maleic anhydride. The polymerization reaction may comprise an initiator, and for example, azobis(isobutyronitrile) (AIBN) can be employed. Preferably, the photosensitive copolymer of formula 3 thus obtained has a weight average molecular weight of 3,000 to 100,000 and a dispersity of 1.0 to 5.0.

Also, the preparation of the photosensitive terpolymers represented by formulae 4 and 5 according to the present invention follows the following schemes 5 and 6, respectively:

[Scheme 5]

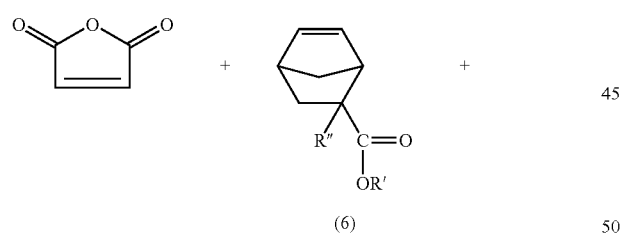

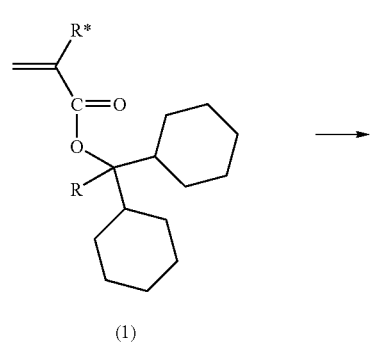

-continued

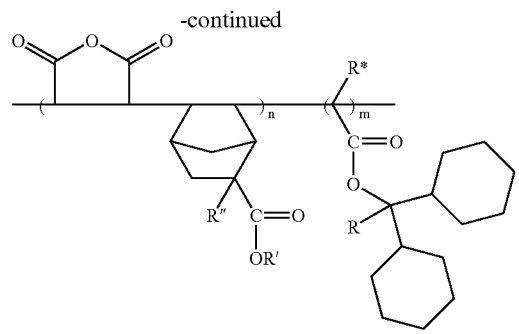

(4)

[Scheme 6]

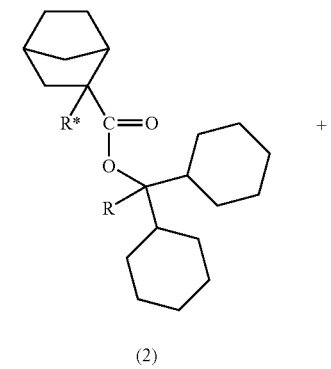

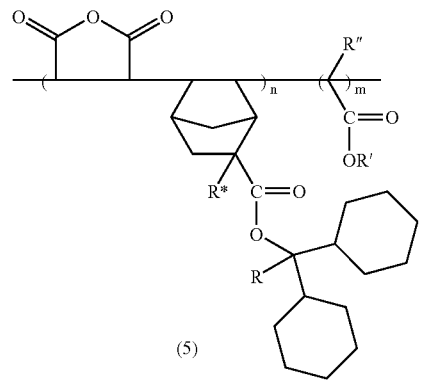

(5)

wherein R, R*, R', and R" are as defined above.

As shown in scheme 5 above, the photosensitive terpolymer of formula 4 of the present invention can be obtained by polymerizing the compound of formula 1 and the norbornene compound of formula 6 together with a maleic anhydride.

Also, as shown in scheme 6 above, the photosensitive terpolymer of formula 5 of the present invention can be obtained by polymerizing the compound of formula 2 and the acrylate compound of formula 7 together with a maleic anhydride.

The above polymerization reactions for the photosensitive terpolymers of formulae 4 and 5 may all comprise an initiator, and for example, azobis(isobutyronitrile) (AIBN) can be employed. Preferably, each of the photosensitive terpolymers of formulae 4 and 5 thus obtained has a weight average molecular weight of 3,000 to 100,000 and a dispersity of 1.0 to 5.0.

Also, the present invention provides a chemically amplified positive photoresist composition for ArF comprising one or more polymers selected from the group consisting of the photosensitive copolymer of formula 3, the photosensitive terpolymer of formula 4, and the photosensitive terpolymer of formula 5.

In the positive photoresist composition of the present invention, the content of one or more polymers selected from the group consisting of the photosensitive copolymer of formula 3, the photosensitive terpolymer of formula 4, and the photosensitive terpolymer of formula 5 is preferably 1 to 30% by weight and more preferably 5 to 8% by weight, based on the total composition.

Further, the photoresist composition of the present invention comprises a photoacid generator and a solvent, if necessary it may be prepared in combination with various additives, and preferably it is prepared such that solid concentration becomes 20 to 50% by weight based on 100 parts by weight of the total resist composition. Thereafter, it is filtered with a 0.2 µm filter and then used.

The content of the photoacid generator is preferably 0.5 to 10% by weight based on the total polymer. As the photoacid generator, there can be used onium salts, organic sulfonic acids, or a mixture thereof.

The solvent used in the present invention includes ethyleneglycolmonomethylethyl, ethyleneglycolmonoethylether, ethyleneglycolmonomethylether, diethyleneglycolmonoethylether, propyleneglycol monomethyl ether acetate (PG-MEA), toluene, xylene, methylethylketone, cyclohexanone, ethyl 2-hydroxypropionate, ethyl 2-hydroxy 3-methyl propionate, ethyl ethoxyacetate, ethyl hydroxyacetate, methyl 2-hydroxy 3-methyl butanoate, methyl 3-methoxy 2-methyl propionate, ethyl 3-ethoxypropionate, ethyl 3-methoxy 2-methyl propionate, ethyl 3-ethoxypropionate, ethyl 3-methoxy 2-methyl propionate, ethyl acetate, butyl acetate, etc.

Furthermore, the resist composition of the present invention may further comprise an organic base, which may be comprised in an amount of 0.01 to 2.00% by weight. As the organic base, there can be used triethylamine, triisobutylamine, triisooctylamine, diethanolamine, triethanolamine or a mixture thereof.

Also, the present invention can provide a semiconductor device having an excellent pattern by coating the above resist composition on a silicon wafer or aluminum substrate using a spin coater to form a resist film and by performing exposure to light, development, and baking processes. As the developing solution, there can be employed an aqueous alkali solution where alkaline compounds such as sodium hydroxide, potassium hydroxide, sodium carbonate, and tetramethylammoniumhydroxide (TMAH) are dissolved at a concentration of 0.1 to 10%. Further, a water-soluble, organic solvent such as methanol and ethanol and a surfactant may be added in a suitable amount to the above developing solution. After development with the developing solution, the film is rinsed with ultra-pure water.

Now, the present invention is described in detail with reference to the following examples. The present invention, however, should not be construed to be limited to these examples.

EXAMPLES

Example 1-1

Synthesis of 1-Methyl-1-Dicyclohexyl (Meth)acrylate (R=Methyl) (Compound 1)

a) Preparation of 1-Methyl-1-Dicyclohexyl Alcohol

210 Ml (0.64 mol) of diethyl ether solution (3.0 M) of methyl magnesium bromide was diluted with 200 ml of anhydrous THF. The solution was then charged into a 1 l flask and the temperature was maintained at 0° C. Dicyclohexyl ketone (62.2 g, 0.32 mol) was slowly dropped into the above solution via a dropping funnel and then reaction was performed at room temperature for about 2 hours. After the reaction was complete, excess THF was removed using a rotary evaporator, and the reaction product was neutralized with a diluted sulfuric acid, extracted using diethyl ether, and dried over magnesium sulfate anhydride. The obtained product was purified by column chromatography to give the title compound, 1-methyl-1-dicyclomethyl alcohol (yield: 90%).

b) Synthesis of 1-Methyl-1-Dicyclohexyl Acrylate

1-Methyl-1-dicyclomethyl alcohol (56.8 g, 0.27 mol) prepared in above a) and triethylamine (44.48 ml, 0.32 mol) were dissolved in 250 ml of THF, and then acryloyl chloride (26 ml, 0.32 mol) was slowly dropped thereinto via a dropping funnel. Then, reaction was performed at room temperature for 2 hours. After the reaction was complete, excess THF was removed using a rotary evaporator and the product was poured into water. Thereafter, the resulting product was neutralized with diluted hydrochloric acid, extracted using diethyl ether, and dried over magnesium sulfate anhydride. The obtained product was purified by column chromatography (n-hexane:ethyl acetate=4:1) to give the title compound, 1-methyl-1-dicyclohexyl acrylate (yield: 70%).

c) Synthesis of 1-Methyl-1-Dicyclohexyl Methacrylate

The procedures were performed in the same manner as in above b), except that methacryloyl chloride was used instead of acryloyl chloride, to prepare 1-methyl-1-dicyclohexyl methacrylate.

Example 1-2

Synthesis of 2-Methyl-2-Dicyclohexyl-5-Norbornene-2-Carboxylate (R=Methyl) (Compound 2)

1-Methyl-1-dicyclohexylacrylate prepared in above Example 1-1, b) (42.3 g, 0.16 mol) was dissolved in 250 ml of THF, cyclopentadiene (31.68 g, 0.48 mol) was slowly added thereto at 0° C., and then the reaction temperature was raised to room temperature. Thereafter, the reaction was performed while stirring at room temperature for 24 hours. After the reaction was complete, excess THF was removed using a rotary evaporator and the reaction product was subjected to vacuum distillation to give the title compound, 2-methyl-2-dicyclohexyl-5-norbornene-2-carboxylate in the state of a viscous colorless liquid (yield: 70%).

Example 1-3

Synthesis of 1-Ethyl-1-Dicyclohexyl (Meth)acrylate (R=Ethyl) (Compound 1)

The procedures were performed in the same manner as in above Example 1-1, a), except that 1.0 M diethyl ether solution of ethyl magnesium chloride was used instead of 3.0 M diethyl ether of methyl magnesium chloride, to prepare 1-ethyl-1-dicyclohexyl acrylate and 1-ethyl-1-dicyclohexyl methacrylate, respectively.

Example 1-4

Synthesis of 2-Ethyl-2-Dicyclohexyl-5-Norbornene-2-Carboxylate (R=Ethyl) (Compound 2)

The procedures were performed in the same manner as in above Example 1-2 except that 1-ethyl-1-dicyclohexyl acrylate prepared in Example 1-3 was used instead of 1-methyl-1-dicyclohexyl acrylate prepared in Example 1-1.

Example 2-1

Synthesis of Copolymer (Compound 3) Using 2-Methyl-2-Dicyclohexyl-5-Norbornene-2-Carboxylate 33.7 G (0.102 mol) of 2-methyl-2-dicyclohexyl-5-norbornene-2-carboxylate prepared in Example 1-2, 10.0 g (0.102 mol) of maleic anhydride, and 0.7 g of azobis(isobutyronitrile) (AIBN) were dissolved in 25 g of anhydrous THF, and the reactants were degassed using an ampoule by a freezing method. The reactants were then polymerized at 68° C. for 24 hours. After the polymerization was complete, the reactants were slowly dropped into excess diethyl ether to precipitate, dissolved again in THF, and reprecipitated in diethyl ether to obtain a copolymer (yield: 40%).

The weight average molecular weight and polydispersity of the obtained copolymer were 8,000 and 1.80, respectively.

Example 2-2

Synthesis of Copolymer (Compound 3) using 2-Ethyl-2-Dicyclohexyl-5-Norbornene-2-Carboxylate The polymerization was conducted in the same manner as in Example 2-1 except that 2-ethyl-2-dicycloehexyl-5-norbornene-2-carboxylate prepared in Example 1-4 was used to prepare a copolymer.

The weight average molecular weight and polydispersity of the obtained copolymer were 7,000 and 1.85, respectively.

Example 3-1

Synthesis of Terpolymer (R=Methyl) (Compound 4)

Except that 1-methyl-1-dicyclohexyl acrylate and 1-methyl-1-dicyclohexyl metharylate were used respectively, a terpolymer consisting of 1-methyl-1-dicyclohexyl acrylate or 1-methyl-1-dicyclohexyl methacrylate was prepared in the following manner.

a) Synthesis of Terpolymer (R=Methyl, $R_3$=Hydrogen)

53.9 G (0.204 mol) of 1-methyl-1-dicyclohexyl acrylate prepared in Example 1-1, 14.1 g (0.102 mol) of 5-norbornene-2-carboxylic acid, 10.0 g (0.102 mol) of maleic anhydride, and 0.7 g of azobis(isobutyronitrile) (AIBN) were dissolved in 50 g of anhydrous THF, and the reactants were degassed using an ampoule by a freezing method. The reactants were then polymerized at 68° C. for 24 hours. After the polymerization was complete, the reactants were slowly dropped into excess diethyl ether to precipitate, dissolved again in THF, and reprecipitated in diethyl ether to obtain a terpolymer (yield: 40%).

The weight average molecular weight and polydispersity of the obtained terpolymer were 7,000 and 1.8, respectively.

b) Synthesis of Terpolymer (R=Methyl, $R_3$=Hydroxyethyl)

The polymerization was conducted in the same manner as in Example 3-1, a) except that 2-hydroxyethyl-5-norbornene-2-carboxylate was used instead of 5-norbornene-2-carboxylic acid to prepare a terpolymer.

The weight average molecular weight and polydispersity of the obtained terpolymer were 8,000 and 1.8, respectively.

c) Synthesis of Terpolymer (R=Methyl, $R_3$=Methyl)

The polymerization was conducted in the same manner as used in Example 3-1, a) except that methyl-5-norbornene-2-carboxylate was used instead of 5-norbornene-2-carboxylic acid to prepare a terpolymer.

The weight average molecular weight and polydispersity of the obtained terpolymer were 8,000 and 1.8, respectively.

Example 3-2

Synthesis of Terpolymer (R=Ethyl) (Compound 4)

Except that 1-ethyl-1-dicyclohexyl acrylate and 1-ethyl-1-dicyclohexyl methacrylate were used respectively, a terpolymer consisting of 1-ethyl-1-dicyclohexyl acrylate or 1-ethyl-1-dicyclohexyl methacrylate was prepared in the following manner.

a) Synthesis of Terpolymer (R=Ethyl, $R_3$=Hydrogen)

The polymerization was conducted in the same manner as in Example 3-1, a) except that 1-ethyl-1-dicyclohexyl methacrylate prepared in Example 1-3 was used instead of 1-methyl-1-dicyclohexyl methacrylate to prepare a terpolymer.

The weight average molecular weight and polydispersity of the obtained terpolymer were 6,500 and 1.8, respectively.

b) Synthesis of Terpolymer (R=Ethyl, $R_3$=Hydroxyethyl)

The polymerization was conducted in the same manner as in Example 3-2, a) except 2-hydroxyethyl-5-norbornene-2-carboxylate was used instead of 5-norbornene-2-carboxylic acid to prepare a terpolymer.

The weight average molecular weight and polydispersity of the obtained terpolymer were 8,000 and 1.8, respectively.

c) Synthesis of Terpolymer (R=Ethyl, $R_3$=Methyl)

The polymerization was conducted in the same manner as in Example 3-2, a) except that methyl-5-norbornene-2-carboxylate was used instead of 5-norbornene-2-carboxylic acid to prepare a terpolymer.

The weight average molecular weight and polydispersity of the obtained terpolymer were 8,500 and 1.8, respectively.

Example 4-1

Synthesis of Terpolymer (Compound 5)

a) Synthesis of Terpolymer (R=Methyl, $R_3$=Hydrogen)

33.7 G (0.102 mol) of 2-methyl-2-dicyclohexyl-5-norbornene-2-carboxylate prepared in Example 1-2, 0.44 g (0.005 mol) of methacrylic acid, 10.0 g (0.102 mol) of maleic anhydride, and 0.7 g of azobis(isobutyronitrile) (AIBN) were dissolved in 25 g of anhydrous THF, and the reactants were degassed using an ampoule by a freezing method. The reactants were then polymerized at 68° C. for 24 hours. After the polymerization was complete, the reactants were slowly dropped into excess diethyl ether to precipitate, dissolved again in THF, and reprecipitated in diethyl ether to obtain a terpolymer (yield: 40%).

The weight average molecular weight and polydispersity of the obtained terpolymer were 8,500 and 1.8, respectively.

b) Synthesis of Terpolymer (R=Methyl, $R_3$=Hydroxyethyl)

The polymerization was conducted in the same manner as in Example 4-1, a) except that 2-hydroxyethyl methacrylate was used instead of methacrylic acid to prepare a terpolymer.

The weight average molecular weight and polydispersity of the obtained terpolymer were 8,000 and 1.8, respectively.

c) Synthesis of Terpolymer (R=Methyl, $R_3$=Methyl)

The polymerization was conducted in the same manner as in Example 4-1, a) except that methyl methacrylate was used instead of methacrylic acid to prepare a terpolymer.

The weight average molecular weight and polydispersity of the obtained terpolymer were 8,000 and 1.8, respectively.

Example 4-2

Synthesis of Terpolymer (Compound 5)

a) Synthesis of Terpolymer (R=Ethyl, $R_3$=Hydrogen)

The polymerization was conducted in the same manner as in Example 4-1, a) except that 2-ethyl-2-dicyclohexyl-5-norbornene-2-carboxylate prepared in Example 14 was used instead of 2-methyl-2-dicyclohexyl-5-norbornene-2-carboxylate to prepare a terpolymer.

The weight average molecular weight and polydispersity of the obtained terpolymer were 8,500 and 1.8, respectively.

b) Synthesis of Terpolymer (R=Ethyl, $R_3$=Hydroxyethyl)

The polymerization was conducted in the same manner as in Example 4-2, a) except that 2-hydroxyethyl methacrylate was used instead of methacrylic acid to prepare a terpolymer.

The weight average molecular weight and polydispersity of the obtained terpolymerwere 8,500 and 1.8, respectively.

c) Synthesis of Terpolymer (R=Ethyl, $R_3$=Methyl)

The polymerization was conducted in the same manner as in Example 4-2, a) except that methyl methacrylate was used instead of methacrylic acid to prepare a terpolymer.

The weight average molecular weight and polydispersity of the obtained terpolymerwere 8,500 and 1.8, respectively.

Example 5

Preparation of Resist Composition 2.0 G of copolymer prepared in Example 2-1 and 0.02 g of triphenyl sulfonium triflate (TPS-105) were completely dissolved in 17 g of propyleneglycol monomethyl ether acetate (PGMEA). The solution was then filtered with a disc filter of 0.2 µm to give a resist composition. Then, the resist solution was coated on the silicon wafer which was treated with hexamethyldisilazane (HMDS), to a thickness of about 0.30 µm.

The silicon wafer having the resist composition coated thereon was pre-baked at 110° C. for 90 seconds and exposed to light using an ArF excimer laser having a numerical aperture of 0.60. Then, post exposure baking (PEB) was performed at 130° C. for 90 seconds.

Thereafter, the resultant was developed using 2.38% by weight of tetramethylammonium hydroxide (TMAH) solution for 30 seconds. As a result, when exposure doses were about 20 mJ/cm$^2$, it was observed that 0.13 µm equal line and space patterns of a rectangular shape were obtained. The copolymer of the present invention reduced the etching rate against polysilicon by 20%, thereby exhibiting excellent etching resistance as compared with conventional COMA.

Example 6

Preparation of Resist Composition 2.0 G of terpolymer prepared in Example 3-1 and 0.02 g of triphenyl sulfonium triflate (TPS-105) were completely dissolved in 17 g of propyleneglycol monomethyl ether acetate (PGMEA). The subsequent procedures were performed in the same manner as in Example 5 to form a resist pattern from the solution. The resist pattern exhibited 0.12 µm equal line and space patterns of a rectangular shape.

Example 7

Preparation of Resist Composition 2.0 G of terpolymer prepared in Example 4-1 and 0.02 g of triphenyl sulfonium triflate (TPS-105) were completely dissolved in 17 g of propyleneglycol monomethyl ether acetate (PGMEA). The subsequent procedures were performed in the same manner as in Example 5 to form a resist pattern from the solution. The resist pattern exhibited 0.12 µm equal line and space patterns of a rectangular shape.

Figure 2:
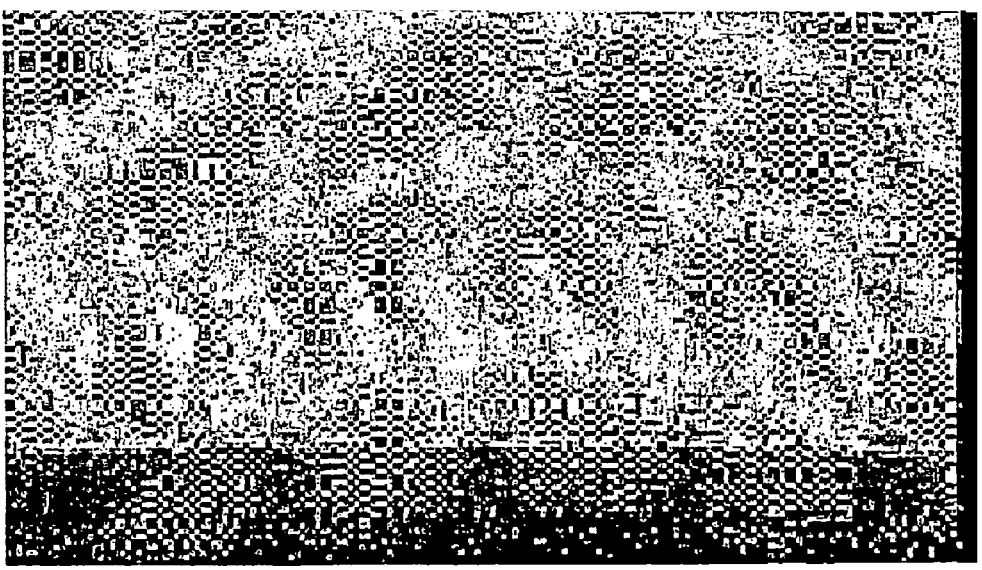
FIG. 2 illustrates a pattern result of a prior COMA-type resist.
Figure 3:
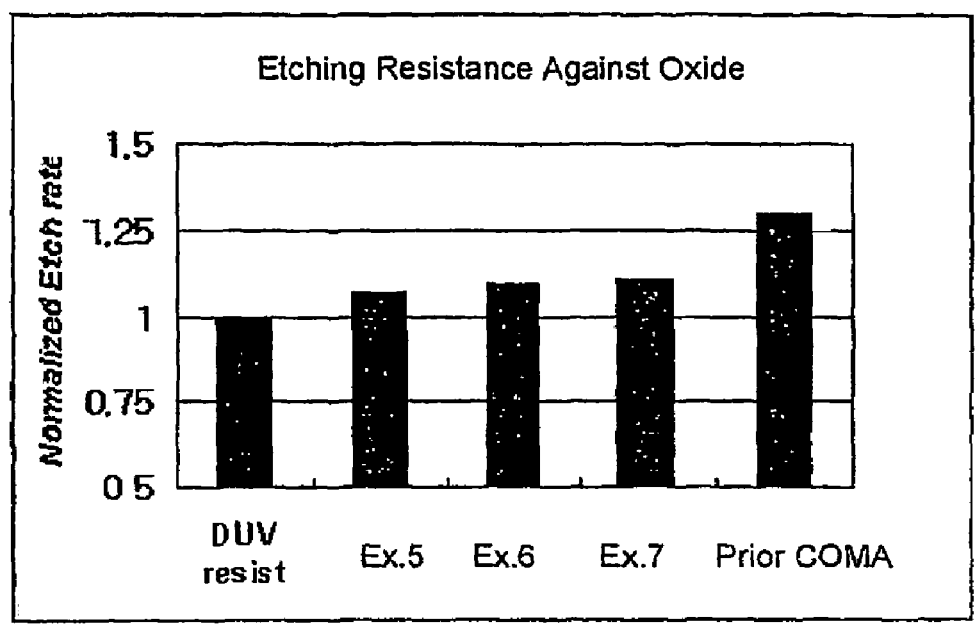
FIG. 3 illustrates etching resistance results against oxides of Examples 5 to 7 according to the present invention.
Figure 4:
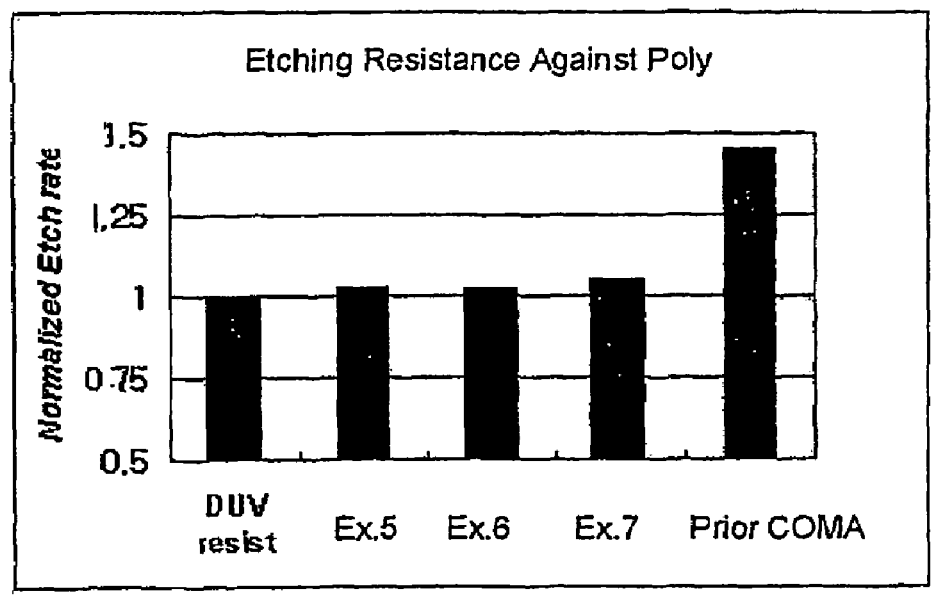
FIG. 4 illustrates etching resistance results against poly of prior COMA-type resists.

The sensitivities, resolutions and pattern shapes of above Examples 5 to 7 and the previously-used COMA type resists are shown in Table 1 below. In addition, Example 7 and the prior COMA resist patterns are shown in FIG. 1 and FIG. 2, respectively. Also, FIG. 3 and FIG. 4 illustrate etching resistance results against oxide and poly, respectively, of Examples 5 to 7 of the present invention and the previously-used COMA-type resists.

TABLE 1

| | Sensitivity (mJ/cm$^2$) | Resolution (µm) | Pattern Shape |
|---|---|---|---|
| Example 5 | 20 | 0.13 | Rectangular |
| Example 6 | 22 | 0.12 | Rectangular |
| Example 7 | 19 | 0.12 | Rectangular |
| Prior COMA | 25 | 0.14 | tapered |

From Table 1 and FIG. 1 to FIG. 4, it can be seen that the resists according to the present invention are excellent in that their pattern shapes are rectangular and they are also excellent in etching resistance against oxides and etching resistance against poly, as compared with the prior COMA.

As described in the above, the present invention can provide a copolymer and terpolymer using a novel (meth) acrylic compound or norbornene carboxylate compound having a pendent group with dicyclohexyl bonded thereto, and it can also provide a chemically amplified positive photoresist composition for ArF which exhibits high resolution and excellent etching resistance due to the use of said polymer, thereby enabling excellent resist patterns to be obtained.

What is claimed is:

1. 1-Alkyl-1-dicyclohexyl (meth)acrylate represented by the following formula 1:

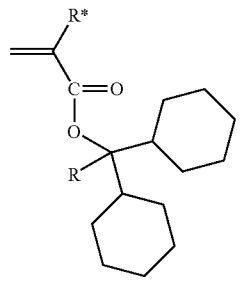

[Formula 1]

wherein R is an ethyl group, and R* is a hydrogen or a methyl group.

2. A process for the preparation of 1-alkyl-1-dicyclohexyl (meth)acrylate of formula 1 as described in claim 1, comprising the steps of:
   a) preparing 1-alkyl-1-dicyclohexyl alcohol by the reaction of dicyclohexyl ketone and an alkyl Grignard reagent or alkyl lithium reagent; and
   b) reacting the 1-alkyl-1-dicyclohexyl alcohol prepared above with (meth)acryloyl chloride.

3. 2-Alkyl-2-dicyclohexyl-5-norbornene-2-carboxylate represented by the following formula 2:

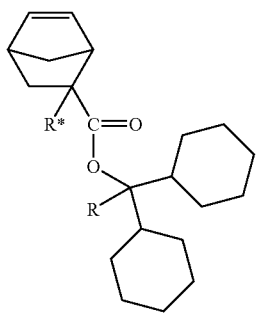

[Formula 2]

wherein R is a methyl or ethyl group, and R is a hydrogen or a methyl group.

4. A process for the preparation of 2-alkyl-2-dicyclohexyl-5-norbornene-2-carboxylate of formula 2 as described in claim 3, by the Diels-Alder reaction of 1-alkyl-1-dicyclohexyl(meth)acrylate of formula 1 as described in claim 1 and cyclopentadiene.

5. A photosensitive copolymer represented by the following formula 3:

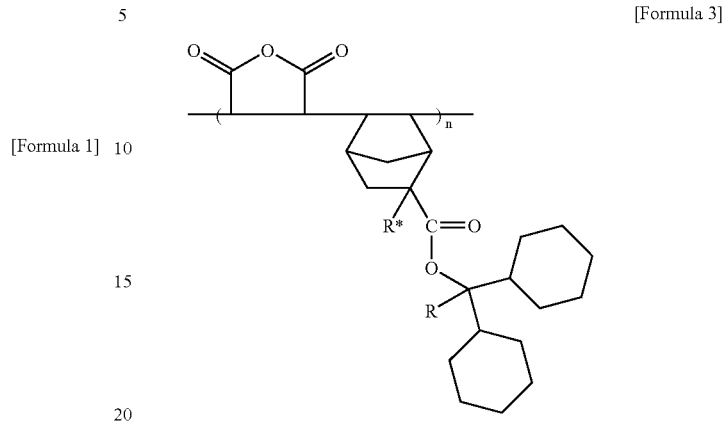

[Formula 3]

wherein R is a methyl or ethyl, R* is a hydrogen or a methyl, and n is an integer of 20 to 25.

6. A process for the preparation of the photosensitive copolymer of formula 3 as described in claim 5, comprising the step of polymerizing the compound of formula 2 as described in claim 3 with a maleic anhydride.

7. A photosensitive terpolymer represented by the following formula 4:

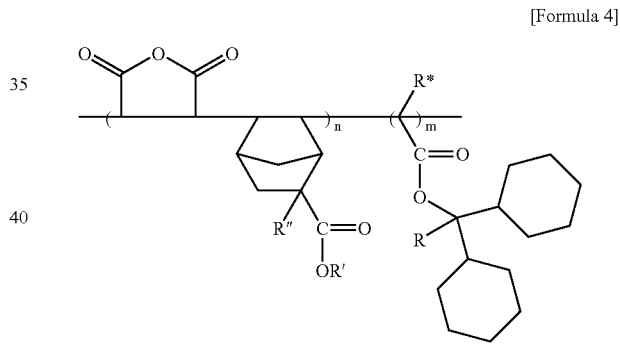

[Formula 4]

wherein R is an ethyl group; R* is a hydrogen or a methyl group; R' is a hydrogen, an alkyl group, or a hydroxyalkyl group; R" is a hydrogen or a methyl group; and m and n each satisfy the conditions m+n=1, 0.1<m<0.9, and 0.1<n<0.9.

8. A process for the preparation of the photosensitive terpolymer of formula 4 as described in claim 7, comprising the step of polymerizing the compound of formula 1 as described in claim 1 with a maleic anhydride and a norbornene compound of the following formula 6:

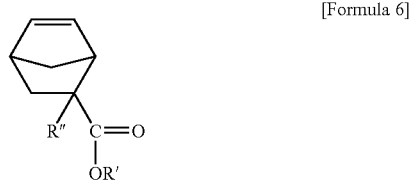

[Formula 6]

wherein R' is a hydrogen, an alkyl group, or a hydroxyalkyl group, and R" is a hydrogen or a methyl group.

9. A photosensitive terpolymer represented by the following formula 5:

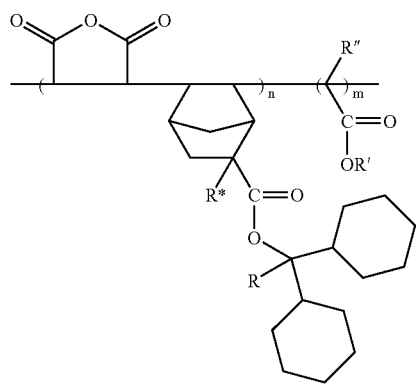

[Formula 5]

wherein R is a methyl or ethyl group; R* is a hydrogen or a methyl group; R' is a hydrogen, an alkyl group, or a hydroxyalkyl group; R" is a hydrogen or a methyl group; and m and n each satisfy the conditions m+n=1, 0.1<m<0.9, and 0.1<n<0.9.

10. A process for the preparation of the photosensitive terpolymer of formula 5 as described in claim 9, comprising the step of polymerizing the compound of formula 2 as described in claim 3 with a maleic anhydride and an acrylate compound of the following formula 7:

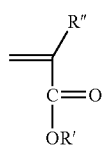

[Formula 7]

wherein R' is a hydrogen, an alkyl group, or a hydroxyalkyl group, and R" is a hydrogen or a methyl group.

11. A chemically amplified positive photoresist composition for ArF comprising one or more polymers selected from the group consisting of the photosensitive copolymer of the following formula 3, the photosensitive terpolymer of the following formula 4, and the photosensitive terpolymer of the following formula 5:

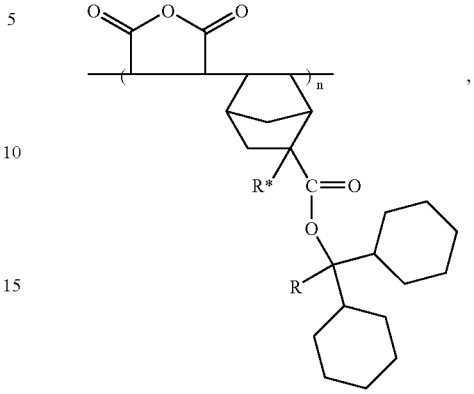

[Formula 3]

wherein R is a methyl or an ethyl group; R* is a hydrogen or a methyl group;

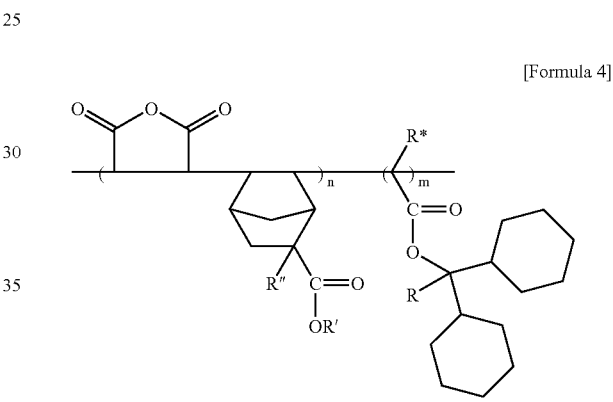

[Formula 4]

wherein R is an ethyl group; R* is a hydrogen or a methyl group; R' is a hydrogen, an alkyl group, or a hydroxyalkyl group; R" is a hydrogen or a methyl group; and m and n each satisfy the conditions m+n=1, 0.1<m<0.9, and 0.1<n<0.9; and

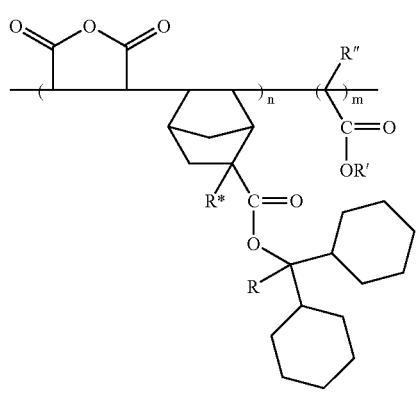

[Formula 5]

wherein R is a methyl or ethyl group; R* is a hydrogen or a methyl group; R' is a hydrogen, an alkyl group, or a hydroxyalkyl group; R" is a hydrogen or a methyl group; and m and n each satisfy the conditions m+n=1, $0.1<m<0.9$, and $0.1<n<0.9$.

12. The positive photoresist composition according to claim 11, characterized in that the content of said polymers is 1 to 30% by weight based on the total composition.

13. The positive photoresist composition according to claim 11, characterized in that said photoresist composition further comprises a photoacid generator in an amount of 0.5 to 10% by weight of the total polymer.

14. The positive photoresist composition according to claim 13, characterized in that said photoacid generator is selected from the group consisting of onium salts, organic sulfonic acids, and a mixture thereof.

15. The positive photoresist composition according to claim 11, characterized in that said photoresist composition further comprises an organic base selected from the group of triethylamine, triisobutylamine, triisooctylamine, diethanolamine, triethanolamine, and a mixture thereof, in an amount of 0.01 to 2.00% by weight of the total polymer.

16. A semiconductor device prepared comprising the positive photoresist composition for ArF as described in claim 11.

* * * * *